United States Patent [19]

Sieber et al.

[11] Patent Number: 5,304,113
[45] Date of Patent: Apr. 19, 1994

[54] METHOD OF ERADICATING INFECTIOUS BIOLOGICAL CONTAMINANTS

[75] Inventors: Fritz Sieber, Brookfield; Orla M. Smith, Milwaukee, both of Wis.

[73] Assignee: The MCW Research Foundation, Inc., Milwaukee, Wis.

[21] Appl. No.: 608,458

[22] Filed: Nov. 2, 1990

Related U.S. Application Data

[63] Continuation-in-part of Ser. No. 477,285, Feb. 8, 1990, Pat. No. 5,039,483, which is a continuation-in-part of Ser. No. 24,150, Mar. 10, 1987, Pat. No. 4,915,683, which is a continuation-in-part of Ser. No. 933,697, Nov. 21, 1986, Pat. No. 4,775,625.

[51] Int. Cl.$^5$ .............................................. A61M 37/00
[52] U.S. Cl. ................................................ 604/4; 604/20
[58] Field of Search ....................... 604/4, 5, 6, 19, 27, 604/48, 49, 20

[56] References Cited

U.S. PATENT DOCUMENTS

| | | | |
|---|---|---|---|
| 3,110,308 | 11/1963 | Bellamy, Jr. | 128/214 |
| 3,140,716 | 7/1964 | Harrison et al. | 128/399 |
| 4,321,919 | 3/1982 | Edelson | 128/214 R |
| 4,398,906 | 8/1983 | Edelson | 604/6 |
| 4,424,201 | 1/1984 | Valinsky et al. | 424/3 |
| 4,428,744 | 1/1984 | Edelson | 604/6 |
| 4,464,166 | 8/1984 | Edelson | 604/6 |
| 4,568,328 | 2/1986 | King | 604/6 |
| 4,573,960 | 3/1986 | Goss | 604/6 |
| 4,573,961 | 3/1986 | King | 604/6 |
| 4,573,962 | 3/1986 | Troutner | 604/6 |
| 4,578,056 | 3/1986 | King et al. | 604/6 |
| 4,596,547 | 6/1986 | Troutner | 604/4 |
| 4,623,328 | 11/1986 | Hartranft | 604/4 |
| 4,651,739 | 3/1987 | Oseroff et al. | 128/395 |
| 4,727,027 | 2/1988 | Wiesehahn et al. | 435/173 |
| 4,748,120 | 5/1988 | Wiesehahn | 435/173 |
| 4,846,788 | 7/1989 | Heitz et al. | 604/20 |

FOREIGN PATENT DOCUMENTS 0196515 1/1963 European Pat. Off.

OTHER PUBLICATIONS

*Journal of Cellular Physiology*, 116: 118-124 (1983), "Susceptability to Merocyanine 540-Mediated Photosensitization: A Differentiation Marker on Murine Hematopietic Progenitor Cells," Richard C. Meagher, Fritz Sieber, and Jerry L. Spivak.

*Proc. Natl. Acad. Sci. USA*, vol. 81, pp. 7584-7587, Dec. 1984, Medical Sciences, "Selective killing of leukemic cells by merocyanine 540-mediated photosensitization," Fritz Sieber, Jerry L. Spivak, and Allison M. Sutcliffe.

*Molecular Basis of Cancer, Part B: Macromolecular Recognition, Chemotherapy, and Immunology*, pp. 227-234, 1985, Alan R. Liss, Inc., "Merocyanine 540-Mediated Photosensitization of Leukemia and Solid Tumor Cells," Fritz Sieber.

*Cancer Research*, 46, pp. 2072-2076, Apr. 1986, "Dye-mediated Photosensitization of Murine Neuroblastoma Cells," Fritz Sieber aand Maya Sieber-Blum.

*Blood*, vol. 68, No. 1 (Jul.) 1986, pp. 32-36, "DyeMediated Photolysis of Human Neuroblastoma Cells: Implications for Autologous Bone Marrow Transplantation," Fritz Sieber, Sanjay Rao, Scott D. Rowley, and Maya Sieber-Blum.

*Minimal Residual Disease in Acute Leukemia*, 1986, A. Habenbeek, B. Lowenberg (editors), Martinus Nijhoff Publishers, "Detection and Selective Destruction of Tumor Cells by the Lipophilic Dye, Mercoyanine 540," pp. 282-294, Fritz Sieber.

*Transfusion*, vol. 26, No. 5, 1986, pp. 481-483, "Inactivation of Human T-Cell Lymphotropic Virus, Type III by Heat, Chemicals, and Irradiation," Gerald V. Quinnan, Jr., Martha A. Wells, Alec E. Wittek, Michael A. Phelan, Ronald E. Mayner, Stephen Feinstone, Robert H. Purcell, and Jay S. Epstein.

*Primary Examiner*—Robert A. Hafer
*Assistant Examiner*—Sam Rimell
*Attorney, Agent, or Firm*—Quarles & Brady

[57] ABSTRACT

A method for externally eradicating by inactivation infectious pathogenic contaminants in body tissues, such as blood, so that it can be introduced into an animal comprises admixing the body tissues with an effective, non-toxic amount of a photoactive agent which selectively binds to the contaminant, passing the resulting mixture through an irradiation chamber, and then irradiating the resulting mixture with an effective level of visible light for an effective period of time to eradicate the contaminants.

11 Claims, 1 Drawing Sheet

METHOD OF ERADICATING INFECTIOUS BIOLOGICAL CONTAMINANTS

This invention was made with government support under Federal Grant 5ROI CA-42734-06 awarded by the National Institutes of Health. The government has certain rights in the invention.

RELATED CASES

This application is a continuation-in-part of U.S Ser. No. 477,285 filed Feb. 8, 1990, now U.S. Pat. No. 5,039,483 which was in turn a continuation-in-part of U.S. Ser. No. 24,150 filed Mar. 10, 1987, now U.S. Pat. No. 4,915,683 issued Apr. 10, 1990, which was in turn a contination-in-part of U.S. Ser. No. 933,697 filed Nov. 21, 1986, now U.S. Pat. No. 4,775,625 issued Oct. 4, 1988.

FIELD OF THE INVENTION

The present invention relates generally to the field of microbiology. More particularly, it relates to a photosensitization method for eradicating infectious, pathogenic contaminants from body fluids.

BACKGROUND OF THE INVENTION

Infectious pathogenic contaminants, such as enveloped viruses, can cause human or animal diseases. The inability to effectively inactivate pathogenic viruses without adversely affecting their antigenic properties has made it difficult to make safe, effective vaccines for viral diseases. In addition, the presence of viruses can destroy the utility of valuable food and industrial products.

Heat treatments, the extraction of virus with solvents and detergents, and the treatment with high doses of gamma radiation can be effective means of inactivating viruses. However, those procedures are rigorous and nonspecific and their applicability is limited. As a result there is a need for a simple, effective method for eradicating viruses, such as the Retroviridae comprising a human immunodeficiency virus, by inactivating them.

It also would be useful to have a method of eradicating protozoa, such as *Plasmodium falciparum*, in whole blood and cellular blood products, such as red cells (Chojnacki et al., *New Engl. J. Med.* 279: 984–985, 1968 and Grant et al., *Lancet II:* 469–491, 1960).

The protozoan parasite, *Plasmodium falciparum*, causes the fatal form of human malaria and it is responsible for over one million deaths among African children annually. Although normally transmitted by the bite of a mosquito vector, malaria can also be transmitted through the transfusion of blood from asymptomatic donors.

BRIEF SUMMARY OF THE INVENTION

It is an object of the present invention to disclose a simple, effective method of eradicating infectious foreign, pathogenic contaminants, such as viruses and protozoa, from body tissues, such as body fluids, by inactivating them before the body fluids are introduced into the body of an animal, such as a human.

Other objects will be apparent from the description which follows.

It has now been discovered that infectious, biological contaminants, such as trypanosomal parasites, protozoa, enveloped viruses, and virus-infected cells, can be eradicated from body fluids outside the body prior to introduction of the decontaminated body fluids into the body of an animal by admixing with the body fluid an effective, non-toxic amount of a photoactive or photosensitizing compound having an affinity to be selectively bound to the contaminants, passing the resulting fluid through an irradiation chamber having a predetermined flow path, and irradiating the resulting fluid in the chamber as it passes with an effective level of radiation by exposing it to radiation in visible light spectrum, for an effective period of time so that the radiation penetrates the fluid and the contaminants have been eradicated by inactivating them while maintaining the viability of the body fluids. It also has been discovered that the antigenic properties of viruses are not adversely affected by the method so that they can be used to prepare vaccines.

The method of the invention offers the following advantages:

1. It is selective. It inactivates the contaminants, especially protozoa, protozoan-infected cells, viruses and virus-infected cells, without adversely affecting the viability of the other body fluid components.

2. It is relatively non-toxic and excess photoactive or photosensitizing agent can be easily removed.

3. It uses visible light.

4. It may be effective against contaminants, such as viruses and protozoa, for which routine screening procedures do not yet exist.

The photoactive or photosensitizing agents which are to be used in the method of the present invention are agents which have an affinity to selectively bind to certain components of the contaminants, such as the lipids in enveloped viruses or virus-infected cells, and which do not or bind only minimally to the other components of the body fluids.

The photoactive agents may be porphyrins or hematoporphyrins, such as those disclosed in U.S. Pat. No. 4,649,151 or dyes such as the merocyanine dyes. The agents which are especially preferred for use in the method are merocyanine dyes which are probably non-mutagenic and which have been used in the past as flourescent probes to study the structure and function of biological membranes (Cohen et al. *J. Membr. Biol.*, 19, 1–36 (1974)). The merocyanine dyes, have been shown to undergo transient, voltage-dependent flourescence enhancements in response to electrical stimulation when they are incorporated into excitable membranes (Davila et al., *Nature New Biol.*, 241, 159–160 (1973)). The generation of electrochemical potentials in human (Sims et al., *Biochemistry,* 13 3315-3330 (1974)) and Amphiuma red cell membranes (Hoffman and Laris, *J. Physiol;* 239. 519–552 (1974)), also enhance the fluorescence of some of these dyes. These probes have been successfully used in the detection of leukemic cells, Valinsky et al., U.S. Pat. No. 4,424,201, and more recently for the selective killing of leukemic cells in bone marrow by agent-mediated photosensitization (Sieber et al., *Proc. Natl. Acad. Sci.* U.S.A. Vol 81, pp. 7584-7587 Dec. 1984).

The preferred agents are compounds of the formula

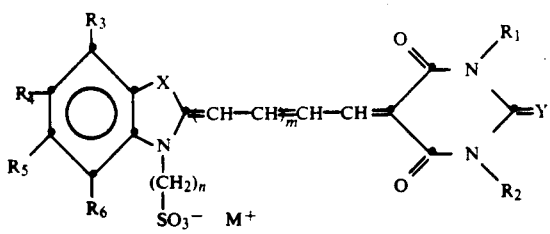

wherein n is 1-5; X is oxygen (O), sulphur (S), —CR$_1$-R$_2$—, or selenium (Se); Y is O or S; M is an alkali metal or other basic group; R1 and R2 are the same or different alkyl groups of 1 to 8 carbons; and R3, R4, R5, and R6 are selected from hydrogen, lower alkyl groups of 1 to 5 carbons, lower alkoxy groups of 1 to 5 carbons, phenyl lower alkyls, such as phenylmethyl; or R3 and R4, or R4 and R5, or R5 and R6 are part of an aromatic ring.

The method of the invention may be practiced on either a continuous basis, or on a batch basis.

The light source for use with the method of the present invention includes any light source that will provide visible light of a suitable wavelength, such as a wavelength range upwards of about 450 nm to about 1000 nm for an effective period of time, including that disclosed in U.S. Pat. No. 4,321,919. Especially preferred is the light source of the photopheresis system available from the THERAKOS Division of Johnson & Johnson Cardiovascular of King of Prussia, Pa., under the trade name UVAR.

The exact mechanism of eradication by inactivation of the contaminants by the method of the present invention is not yet fully understood. The currently available data are compatible with the following model: The photosensitizing agent binds preferentially to disordered or cholesterol-free domains in lipid bilayers. Binding to proteins, carbohydrates and chromatin is minimal. High affinity binding sites for the agent appear to exist on contaminants, e.g. enveloped viruses and some virus-infected cells. Photoexcitation of membrane-bound agent molecules leads to the formation of reactive oxygen species, such as singlet oxygen, which cause lipid peroxidation. Secondary photo-products may react with intracellular components.

Variables which can affect the method are agent concentration, protein concentration, protein composition, geometry and optical properties of the container, intensity and spectral properties of the light source and duration of the illumination. Those skilled in the art will appreciate that each of those variables can be varied within rather wide margins, provided the other variables are adjusted accordingly.

DESCRIPTION OF THE PREFERRED EMBODIMENT

Figure 1:
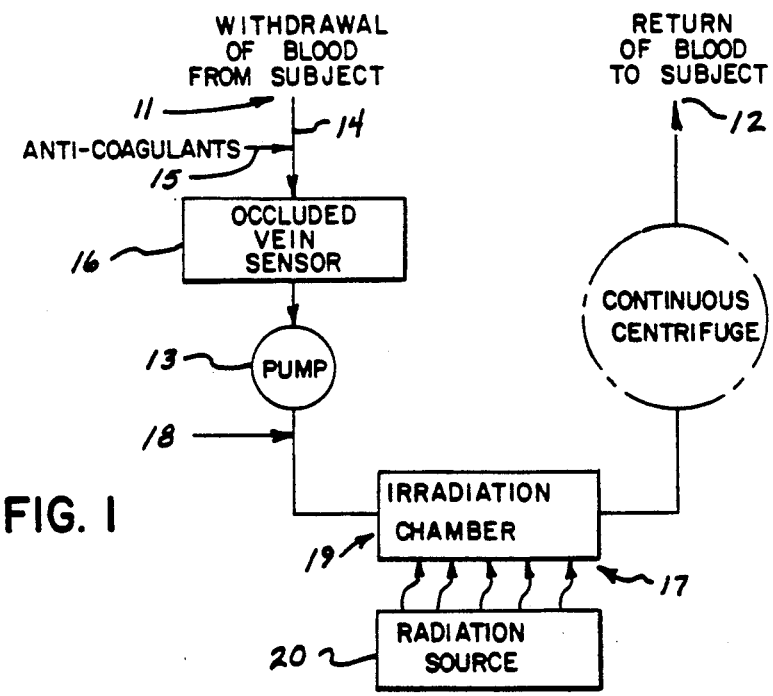
FIG. 1 is a schematic flow diagram illustrating a preferred embodiment of a system operating in accordance with the present invention.

In FIG. 1 herein a schematic diagram is shown of a system 10 for use with the method of the present invention.

As shown schematically in FIG. 1, blood may initially be withdrawn from the patient infected with an infectious pathogenic biological contaminant, as at 11. Typically the blood is withdrawn via a donor needle, which may be placed in the right antecubital vein. In the system 10 of FIG. 1, it is assumed that the processing of blood is conducted on a continuous basis from 11 to a final return of the blood to the subject at 12. The return at 12 is via a recipient needle positioned in the left antecubital vein. Where the method is continuous a typical blood flow is in range of from about 10 to 75 ml/min. with a preferred range being from about 40 to 50 ml/min. The desired flow rates are produced by a pump 13, which is positioned in the extracorporeal blood flow stream generally indicated as 14.

Anti-coagulants are preferably injected into the extra-corporeal blood flow stream at 15, close to the point of blood withdrawal. Such anti-coagulants can comprise solutions of acid, citrate and dextrose and/or heparin, or of other known anti-coagulant compositions. An occluded vein sensor 16 is preferably provided in stream 14 to prevent or inhibit the generation or continued existence of bubbles in the blood flow stream.

In the preferred mode of practicing the continuous mode of the method of the present invention, the photoactive or photosensitizing agent is added to the fluid after it leaves the body. Thus, as shown in the system 10 of FIG. 1, the agent may be added to the flowing blood downstream of pump 13, and just upstream of where the product enters the irradiation station 17.

The photosensitizing agent is usually first dissolved in an isotonic solution, which thereafter is directly injected into the flowing blood stream, as at 18. The agent is injected at a rate which takes into account the blood flow rate and achieves a concentration of the agent in the blood in the desired range as the blood passes through the irradiation station 17.

It will be appreciated that the photosensitizing agent may not need to be directly introduced by injection into the extracorporeal blood stream 14. It also might be possible to obtain the desired concentration of the agent by orally or otherwise administering the compound directly to the patient before removing the blood. Alternate modes of administration of the photosensitizing agents are within the scope of this invention and the doses appropriate therefore will be apparent to those skilled in the art.

The introduction of the photosensitizing agents to the extracorporeal stream is preferred because it makes it possible to achieve more exact concentration levels; and to avoid or minimize possible side effects and the like, which can occur from administration of any drug directly to the body system.

At irradiation station 17, which consists of an irradiation chamber 19 and radiation source 20, the product containing the desired concentration of dissolved photosensitizing agent, is subjected to visible light having a wavelength range upwards of about 400 nm to about 1000 nm and preferably visible light having the bulk of its spectral components in the preferred orange to green range for the activation of the particular photosensitive agent being employed in the treatment being conducted. The irradiation station 19 is constructed so as not to block radiation in the desired portion of the visible light spectrum and to prevent the body fluid from being overheated and damaged.

Figure 2:
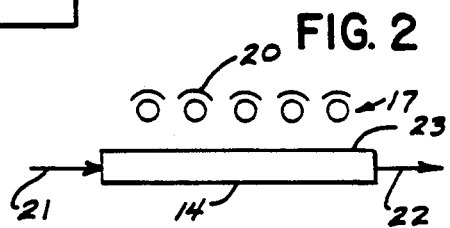
FIG. 2 is a schematic elevational view of the irradiation station portion of the FIG. 1 system.

In FIG. 2, a schematic view appears of an irradiation station 17 of a type suitable for use with the invention. The preferred station 17 consists of an irradiation chamber 19, having an inlet 21 and an outlet 22, enabling product flow through the chamber, and a spaced radiation source 20 of visible light. The chamber 19 can take various forms, with the principal requirement being that it have at least one wall 23 which is substantially transparent to visible light. The chamber (or at least the transparent wall 23) therefore can be comprised of various substantially visible light transparent plastics, such as polyvinyl chloride and the like.

In the irradiation chamber 19, the body fluid to be treated flows through a cell assembly or flow passage which is of relatively thin cross-section e.g. about 2 mm thick if the fluid contains a high concentration of red blood cells. The total surface area of the flow passage in the chamber 19 is calculated to provide the body fluid contained therein with the desired radiation dose level from the visible light source 20. Especially preferred is an apparatus consisting of a plurality of fluorescent tubes with concentric jackets spaced from the tubes to form the flow passages for the body fluid to be irradiated.

The visible light source can comprise commercially available lamps, numerous types of which are known in the art. By way of example, source 20 can comprise a single incandescent or fluorescent lamp or multiple lamps which preferably emit visible light in the orange to green spectrum, i.e., between about 5200 to about 6500 Angstroms, which is preferred when a merocyanine dye is the photo-sensitizing agent being employed in the method of the invention. With the continuous flow rates utilized in accordance with one aspect of the invention, such a source will provide the desired amount of absorbed energy in the flowing blood for practicing the method of the invention.

The blood flow from irradiation station 17 proceeds as shown in FIG. 1 via outlet 22 back to the subject at 12. Optionally, however, prior to returning the treated blood to the patient, it may be heat exchanged so as to adjust its temperature to that of the patient's circulating blood. Heat exchange may be necessary whenever the treated blood, by consequences of its treatment, has attained a temperature substantially at variance with that of the patient.

Alternatively, the apparatus may take the form of a single batch container, containing the product and the photosensitizing agent, which can be treated with visible light.

When the product is in an aqueous environment the preferred excitation spectrum peaks for the merocyanine are at 510 and 535 nm and in an organic phase, the spectrum is redshifted to 565 nm. After completion of the photosensitization step the excess agent may be separated by centrifugation. If desired, undesired components can be separated from the mixture by precipitation with solvents or salt, solvent extractions, or by chromatographic means.

Regardless of which photosensitizing agent is employed in the invention or at what rate it is administered the burden placed upon the body's organ system can be further alleviated, by utilizing in conjunction with the present system, a continuous centrifuge (or other filtration system), which device can be used to separate photosensitizing agents.

Figure 3:
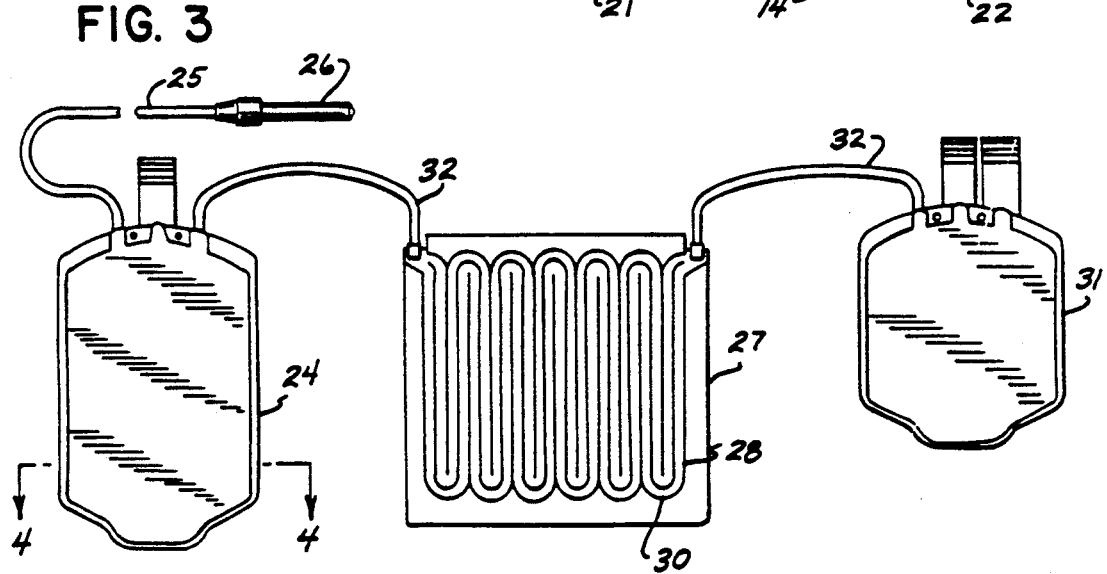
FIG. 3 is a perspective view of a preferred embodiment of an apparatus of the present invention.
Figure 4:
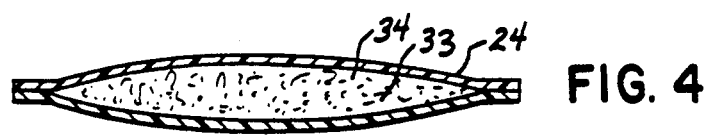
FIG. 4 is a cross-sectional view taken along lines 4—4 of FIG. 3.

The preferred embodiment of the apparatus of the invention which is used when whole blood is collected, treated to inactivate protozoa and stored to be later administered to the donor or another human is shown in FIGS. 3 and 4. The apparatus as seen in FIG. 3 comprises a first container 24, which is provided with collection tubing 25 and a needle 26; an irradiation chamber 27 comprising a flat, plastic envelope 28 with a continuous cell assembly or flow passage 30; a storage container 31; and tubing 32 which connects the first container 24, the irradiation chamber 27 and the storage container 31 into a closed system. The body fluid can be transferred from the container 24 to the irradiation chamber 27 where it is exposed to visible light and maintained at a safe temperature e.g., by a water bath. It is then transferred to the storage container 30. The body fluid can be transferred through the system by squeezing the first container 24 and/or by use of a tubing pump (not shown). Alternatively, the novel apparatus may take the form of a single container, containing the photosensitizing agent, in which the body fluid can be collected, treated with visible light and stored.

In the apparatus of FIG. 3, an effective amount of anticoagulant liquid 33 containing the photosensitizing agent represented by dots 34 is already in the first container 24. Of course, the agent 34 may be added to the apparatus at any time prior to treatment of the whole blood or blood products, such as blood plasma, serum and fluids from plasmapheresis, with the visible light. The apparatus and its contents are preferably agitated to bring the agent into contact with the contaminant in the body fluids before treating the mixture with visible light to inactivate the contaminant. If the body fluid is blood it can then be divided into its various components either before or after addition of the photosensitizing agent and/or exposure to visible light. Any excess photosensitizing agent can, if desired, be removed any time after the light exposure by conventional means.

In those embodiments of the inventions in which the product containing the contaminant to be inactivated is not blood collected directly from a donor, the photosensitizing agent may be added to the product immediately prior to light exposure. For example, when the product is blood cells they are first suspended in a physiological medium and when the product is bone marrow or blood cells, it is preferred to suspend it in deuterium oxide ($D_2O$) because the presence of $D_2O$ shortens the illumination time required, presumably by extending the half life of singlet oxygen. The photosensitizing agent is then added to the solution or suspension and the resulting mixture stirred or otherwise agitated to bring the agent into contact with the contaminant or contaminant-infected cells. The mixture is then exposed to visible light of a suitable wavelength. In an aqueous environment the preferred excitation spectrum peaks for MC 540 are at 510 and 535 nm and in an organic phase, the spectrum is redshifted to 565 nm. Structural analogs may have somewhat different absorption characteristics. After completion of the photosensitization step the excess agent may be separated from the desired blood component by centrifugation, precipitation with solvents or salt, solvent extraction, or by chromatographic or other means. If desired, undesired components such as plasma proteins, can be separated from the mixture by precipitation with solvents or salt, solvent extractions, or by chromatographic means.

Representative of the specific agents that can be used are the following:

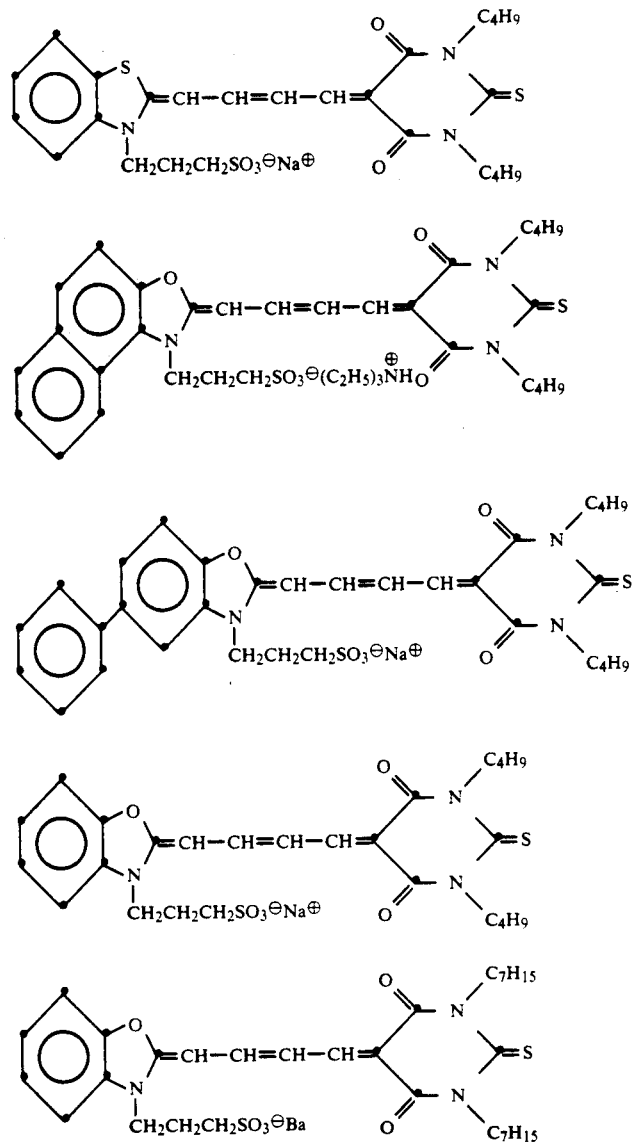

The photoactive or photosensitizing agent is employed in an amount which is effective under the conditions of use to accomplish the inactivation of the contaminants which may be present. Some of the agents, of course, are more active than others and can be used in smaller amounts. The toxicity of the preferred merocyanine dyes is very low. Therefore, it is not essential that they be completely removed from the treated product before it can be used in its normal manner.

The merocyanine, MC 540, is normally used with light of suitable wavelength in an amount of about 10 micrograms to about 25 micrograms per milliliter of product and a more active merocyanine derivative, MC 540A, is used in an amount of about 5 micrograms to about 10 micrograms per milliliter under comparable conditions.

The effective wavelengths of the visible spectrum that can be used vary greatly; however, it is generally desired that the light be of a wavelength in the green to orange range when the agent is a merocyanine dye. It appears that blue light and dark red light is not particularly effective with the preferred merocyanine dyes.

Tests have shown that:

1) Suspensions of Friend virus, Friend virus-transformed cells, Herpes simplex, HTLV-I and HTLV-I infected cells are rapidly inactivated by MC 540-mediated photosensitization.

2) The small amounts of dye that are transferred with the photosensitized products or plasma/serum components are not toxic to mice. The effective amount of the most active merocyanine derivative is about 100,000 times less than the $LD_{10}$ of the compound in mice.

3) Seventy to one hundred percent of mice receiving malarious (P. yoelii) blood which had been treated for 60 minutes with the photosensitizing agent and light survived. In contrast one hundred percent of the mice receiving untreated malarious blood died.

4) The same treatment protocol was much less toxic to mature blood cells and normal pluripotent hematopoietic stem cells in the mouse.

5) Photosensitized plasma clots normally, suggesting that at least some clotting factors are still intact.

6) The small amounts of dye that are transferred with photosensitized red blood cells do not appear be to toxic to mice.

The ability of MC 540 to react with enveloped (i.e. lipid-containing) viruses was tested with the Friend erythroleukemia virus complex, the human T cell leukemia virus, HTLV-I and Herpes simplex 1. Friend virus was obtained from cell-free supernatants of cultured erythroleukemia cells or as a cell-free extract from infected animals. Simultaneous exposure to MC 540 (15 ug/ml) and light (40 $J/cm^2$) reduced the virus titer by $\geq 4$ logs regardless of the origin of the virus preparation. Virus-infected spleen cells, bone marrow cells, and cultured Friend erythroleukemia cells were inactivated at about the same rate as cell-free virus preparations.

HTLV-I was also susceptible to MC 540-mediated photosensitization. The amount of virus that could be sedimented by centrifugation was reduced 5-fold after treatment with MC 540 and light. The remaining 80% of the virus were probably lysed. The small fraction that was sedimented was visibly stained by MC 540. It is conceivable that the sedimented virus fraction, although not lysed, had sustained enough photodynamic damages to make it noninfectious. For example, when the virus is Herpes simplex 1 the order of magnitude reduction is as high as 45 times.

The demonstrated effectiveness of the method of the present invention in inactivating Herpes simplex 1 makes it possible to treat herpes lesions by applying or injecting MC 540 containing preparations onto or into the lesions.

The ability of the agents to photosensitize in such lower concentrations should make it possible to use the dyes or dermatological products which can be painted on in injected into viral containing lesions prior to exposure to visible light.

The simultaneous exposure to MC 540 and visible light also appears to kill protozoan-infected red blood cells very rapidly, but normal pluripotent hematopoietic stem cells and mature blood cells very slowly. This differential sensitivity to MC 540-mediated photolysis may be useful in purging blood and red blood cells of cell-free protozoa and protozoan-infected cells thus making the blood supply safer for use.

An analog of MC 540 which we have labeled MC 540A (see structural formula below) reduces illumination times about 6-fold when used in equimolar concentrations.

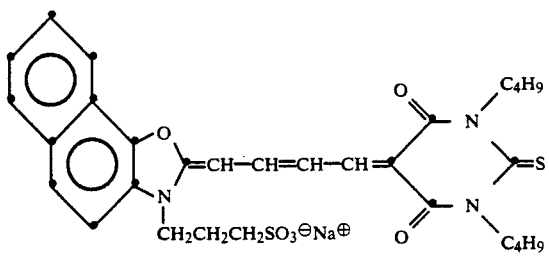

Merocyanine-mediated photolysis of tumor cells, viruses and protozoa appear to be primarily mediated by singlet oxygen. An additional 2-fold reduction in illumination time can therefore be achieved by performing the photosensitization step in the presence of deuterium oxide ($D_2O$).

Unlike heat or high doses of ionizing irradiation, MC 540-mediated photolysis is more selective in its toxicity. Dye-mediated photosensitization may be the preferred anti-viral treatment in situations where critical components are temperature or radiation sensitive. In addition, the acute systemic toxicity of dyes, such as MC 540, is very low. The amount of dye that is injected with a typical mouse bone marrow graft is more than 100,000 times less than the $LD_{10}$ in the same species.

Surprisingly, tests have shown that viruses inactivated by the method of the present invention retain their anti-genic properties. Thus, it should be possible to make vaccines using the viruses inactivated by the method of the present invention.

Representative of the viruses which can be inactivated by the method of the present invention are those previously described, as well as, the viruses which cause human and animal diseases, such as bovine viral diarrhea, and viruses which infect bacterial products such as the Epstein Barr virus.

The invention is further illustrated by the following examples.

EXAMPLE 1

When cultured F4-6 erythroleukemia cells, spleen or marrow cells from diseased animals, cell-free extracts of cultured cells, spleen cells, or marrow cells, or cell-free supernatants of F-6 cultures were injected into healthy B6D2F1 mice, the spleen weights increased from 70 mg to about 2 g within two weeks. The animals became polycythemic and, eventually, died. When cell suspensions, cell-free extracts, or culture supernatants were photosensitized and exposed to light prior to injection, spleen weights remained normal, hematocrits remained normal, and the animals survived. Normal pluripotent hematopoietic stem cells (as determined by the ability of photosensitized marrow cells to rescue lethally irradiated syngeneic hosts) were spared by the photosensitization treatment. Virus preparations that were exposed to dye or light alone caused splenomegaly, polycythemia, and death. A series of experiments thus showed that MC 540-mediated photolysis inactivates free Friend virus, intracellular Friend virus, and Friend virus-infected cells.

EXAMPLE 2

Experiments with human herpes simplex virus type 1 (HSV-1), and human T-cell leukemia virus type I (HTLV-I) produced similar results. Herpes simplex-1 was extremely susceptible to MC 540 mediated photolysis. A limiting dilution plaque forming assay on Vero cells indicated a $\geq 5$ log reduction (limit of detection) of the virus titer after only 10 min. of illumination. The standard illumination protocol calls for 90 min. of illumination. It is thus conceivable that the titer can be reduced by $\geq 45$ log. Infectivity assays for HTLV-I have, unfortunately, not yet been developed. We therefore used reverse transcriptase activity as an indicator of virus destruction. Photosensitized and untreated aliquots of the same virus suspension were pelleted on a sucrose cushion. The pellet of the treated aliquot was about 5 times smaller and visibly red. Its reverse transcriptase content was reduced by more than 80% (Table 1). The balance of the enzyme activity was recovered in the supernatant. More than 80% of the original virus mass was apparently damaged so extensively (virtually "dissolved") that it was no longer pelletable by a two hour spin at 100,000 $\times$ g. If the photosensitization of enveloped viruses bears any resemblance to the photosensitization of cells, it is reasonable to speculate that the pelletable material was also photodamaged and perhaps no longer infective.

TABLE 1

| HTLV-I. Reverse Transcriptase activity | | |
|---|---|---|
| 1) | No dye, no light | 194,268 cpm |
| 2) | MC 540, no light | 208,548 cpm |
| 3) | No dye, light 90 min | 158,016 cpm |
| 4) | MC 540, light 90 min | 37,848 cpm |

EXAMPLE 3

The acute systemic toxicity of MC 540 was determined by injecting groups of 10 BAF1 mice intravenously with graded doses of MC 540. Survival data were plotted on a log probit scale and fitted with a least square regression line to determine $LD_{10}$ and $LD_{50}$ (Table 2). It should be pointed out that MC 540 is not more toxic than the fluorescent dyes that are commonly used for the angiography of the retina. Necropsies showed that the probable cause of death after high doses of MC 540 was the formation of large emboli of precipitated dye in major blood vessel (i.e. we killed the mice by exceeding the solubility of the dye in plasma).

TABLE 2

| Acute Toxicity of MC 540 | |
|---|---|
| $LD_{10}$ (mouse) | 55 mg/kg |
| $LD_{50}$ (mouse) | 84 mg/kg |
| Injected with photosensitized marrow graft | 0.0004 mg/kg |
| For comparison | |
| $LD_{50}$ (mouse) fluorescein | 300 mg/kg |
| $LD_{50}$ (mouse) indocyanine green | 70 mg/kg |

EXAMPLE 4

Using the rodent malaria species, P. yoelii YM, and P. berghei berghei as model systems, the survival of mice i.v. injected with MC 540-treated and non-treated malarious blood was monitored in vivo. Treatment of P. yoelli-infected blood (40%-70% parasitemia) with dye and light for 90 minutes resulted in total protection of the recipient mouse population while 60 minutes of dye/light treatment resulted in survival of 70%-100% of the recipient population. Shorter illumination times provided partial protection. All mice receiving untreated malarious blood died rapidly. In a subsequent experiment, serial dilutions of treated (30 minutes of dye/light) or control malarious blood (30% parasitemia) were injected into recipient mice. One hundred percent of the mice receiving $10^4$ treated cells survived compared to 0% of the corresponding control group. It was observed in both treatments that some of the surviving mice initially showed severe symptoms of malaria (e.g. splenomegaly, anemia) but later recovered. It is conceivable that MC 540 treatment of infected blood enhanced the immune response of the recipient mice.

In two experiments, all mice receiving P. berghei-infected blood (30% parasitemia), treated for 15-45 minutes with light and MC 540, died as did their control counterparts. However, 10% of the group receiving infected blood treated for 60 minutes with light and dye survived for the duration of the experiment (90 days).

P. yoelii preferentially infects mature erythrocytes while P. berghei prefers to invade reticulocytes. The enhanced killing of P. yoelii-infected cells compared to P. berghei-infected cells may reflect a greater susceptibility of erythrocytes (compared to reticulocytes) to MC 540-mediated photoinactivation. P. falciparum invades erythroid cells at all of the later stages of development. However, only 2 of the 4 parasite developmental stages of P. falciparum are found in the peripheral blood and these are at such a low cell density in asymptomatic carriers as to be undetectable in thick or thin smears. In our in vivo experiments, P. yoelii-infected blood with exceedingly high parasitemias representing all stages of development was used and protection by MC 540 treatment was still obtained.

MC 540-sensitized photoirradiation (or photoirradiation sensitized by structural analogs of MC 540) can be useful as a means of eradicating malarially-infected cells by inactivating them in blood or blood products. In addition, this technique can prove useful for purging other blood-borne protozoan parasites, such as Trypanosoma cruzi, the causative organism of Chaga's disease, from the donor blood supply.

It will be appreciated by those skilled in the art that the method of the present invention will make it possible for biologicals, such as pure bacterial cultures, culture mediums and the like to be supplied viral-free.

It is not presently known exactly which contaminants of the many identified can be effectively eradicated by the method of the present invention. However, those skilled in the art should be able to apply the method to specific contaminants without undue experimentation.

It will be readily understood by those skilled in the art that the foregoing description has been for purposes of illustration only and that a number of changes may be made without departing from the scope of the invention. Therefore, it is intended that the invention not be limited except by the claims.

We claim:

1. A method for eradicating infectious pathogenic biological contaminants from body fluids outside the body prior to introduction of the decontaminated body fluids into the body of a patient, said method comprising:

admixing an effective, non-toxic amount of a photoactive compound with the body fluid to product a resulting body fluid, the photoactive compound having an affinity to be selectively bound to the contaminants;

passing the resulting fluid under flow conditions through a cell assembly having a predetermined flow path; and irradiating the resulting fluid in the cell assembly as same passes through the flow path with an effective level of radiation in the region of the visible spectrum, with a wavelength range above 400 nm to about 1000 nm, for an effective period of time such that the radiation penetrates the resulting fluid and exposes the photoactive-compound-bound contaminants to the radiation so as to eradicate such contaminants while maintaining the viability of said body fluids to produce viable decontaminated body fluids.

2. The eradicating method as recited in claim 1 further comprising the step of selecting a body fluid from the group consisting of whole blood, blood plasma, serum, and fluids from plasmapheresis.

3. The eradicating method as recited in claim 1 further comprising the step of selecting body fluids which contain an envelope-containing virus.

4. The eradicating method as recited in claim 1 further comprising the step of selecting body fluids which contain pathogenic biological contaminants comprising a malarial parasite.

5. A method of extracorporeal treatment of the blood of a patient infected with infectious pathogenic biological contaminants said method comprising:

removing blood from the body of a patient infected with infectious pathogenic biological contaminants;

adding to said blood, before the removal of the blood, an effective, non-toxic amount of photoactive compound having an affinity to be selectively bound to the infectious contaminants;

passing said treated blood through a cell assembly having a predetermined flow path;

irradiating said contaminated blood admixed with photoactive compound in the cell assembly as same passes through the flow path with an effective level of radiation in the region of visible spectrum, with a wavelength range 400 nm to about 1000 nm, for an effective period of time such that the radiation penetrates the blood and exposes the photoactive-compound-bound infectious contaminants to the radiation so as to eradicate such infectious contaminants while maintaining the viability of components in said blood to produce a viable and decontaminated blood; and returning said viable and decontaminated blood to the patient's body.

6. The method of claim 5 wherein the level of radiation is produced by a light source having a wavelength of from about 600 to about 1000 nm.

7. The eradicating method as recited in claim 5 further comprising the step of selecting a blood which contains pathogenic biological contaminants comprising an envelope-containing virus.

8. The eradicating method as recited in claim 5 further comprising the step of selecting the Retroviridae comprising a human immunodeficiency virus.

9. The eradicating method as recited in claim 5 further comprising the step of selecting the pathogenic biological contaminants comprising a malarial parasite.

10. The eradicating method as recited in claim 5 further comprising the step of selecting a blood which contains pathogenic biological contaminants comprising a trypanosomal parasite.

11. A method for extracorporeal treatment of the blood of a patient infected with infectious pathogenic biological contaminants, said method comprising:

removing blood from the body of a patient infected with infectious pathogenic foreign biological contaminants;

adding to said blood, after the removal of the blood, an effective non-toxic amount of photoactive compound having an affinity to be selectively bound to the infectious contaminants;

passing said treated blood through a cell assembly having a predetermined flow path;

irradiating said contaminated blood admixed with photoactive compound in the cell assembly as the same passes through the flow path with an effective level of radiation in the region of visible spectrum, with a wavelength range above 400 nm to about 1000 nm, for an effective period of time such that the radiation penetrates the blood and exposes the photoactive-compound-bound infectious contaminants to the radiation so as to eradicate such infectious contaminants while maintaining the viability of compounds in said blood to produce a viable and decontaminated blood; and returning said viable and decontaminated blood to the patient's body.

* * * * *